United States Patent
DeGould

(10) Patent No.: US 8,221,316 B2
(45) Date of Patent: Jul. 17, 2012

(54) SUCTION RETRACTION INSTRUMENT FOR SURGERY

(76) Inventor: Michael D. DeGould, Rockford, IL (US)

(*) Notice: Subject to any disclaimer, the term of this patent is extended or adjusted under 35 U.S.C. 154(b) by 1135 days.

(21) Appl. No.: 11/215,058

(22) Filed: Aug. 30, 2005

(65) Prior Publication Data

US 2007/0060793 A1    Mar. 15, 2007

(51) Int. Cl.
*A61B 1/32* (2006.01)
(52) U.S. Cl. ................... 600/205; 600/237
(58) Field of Classification Search ......... 600/185–187, 600/201–237, 188–200
See application file for complete search history.

(56) References Cited

U.S. PATENT DOCUMENTS

| | | | | |
|---|---|---|---|---|
| 3,626,471 A | * | 12/1971 | Florin | 600/205 |
| 4,049,000 A | | 9/1977 | Williams | |
| 4,883,426 A | | 11/1989 | Ferrer | |
| 4,992,047 A | * | 2/1991 | Warner | 433/91 |
| 5,123,403 A | * | 6/1992 | Lavyne | 600/235 |
| 5,281,134 A | * | 1/1994 | Schultz | 433/29 |
| 5,665,052 A | * | 9/1997 | Bullard | 600/194 |
| 6,083,175 A | * | 7/2000 | Lundgren | 600/562 |
| 6,875,173 B2 | * | 4/2005 | Suddaby | 600/210 |
| 7,150,714 B2 | * | 12/2006 | Myles | 600/205 |
| 2007/0161863 A1 | * | 7/2007 | Bentt | 600/187 |

OTHER PUBLICATIONS

"nozzle." Merriam-Webster Online Dictionary. 2010. Merriam-Webster Online. Jan. 26, 2010 <http://www.merriam-webster.com/dictionary/nozzle>.*

* cited by examiner

*Primary Examiner* — Eduardo C Robert
*Assistant Examiner* — Steven Cotroneo
(74) *Attorney, Agent, or Firm* — Quarles & Brady LLP

(57) ABSTRACT

A combination suction retraction instrument for surgery is disclosed. The suction retraction instrument includes a retractor including a body, a suction nozzle secured to a distal end of the body, and means for retaining a suction tube adjacent the retractor. The suction tube is connected to a vacuum source for removing fluids and debris from a surgical site. The means for retaining the suction tube is secured to the body. The means for retaining the suction tube is structured to allow the suction tube to slide within the means for retaining the suction tube upon manual pulling of the suction tube by a surgeon. A proximal end of the suction nozzle is dimensioned to engage a distal end of the suction tube in a sealing relationship thereby providing a suction flow path from an opening of the suction nozzle into the suction tube.

14 Claims, 2 Drawing Sheets

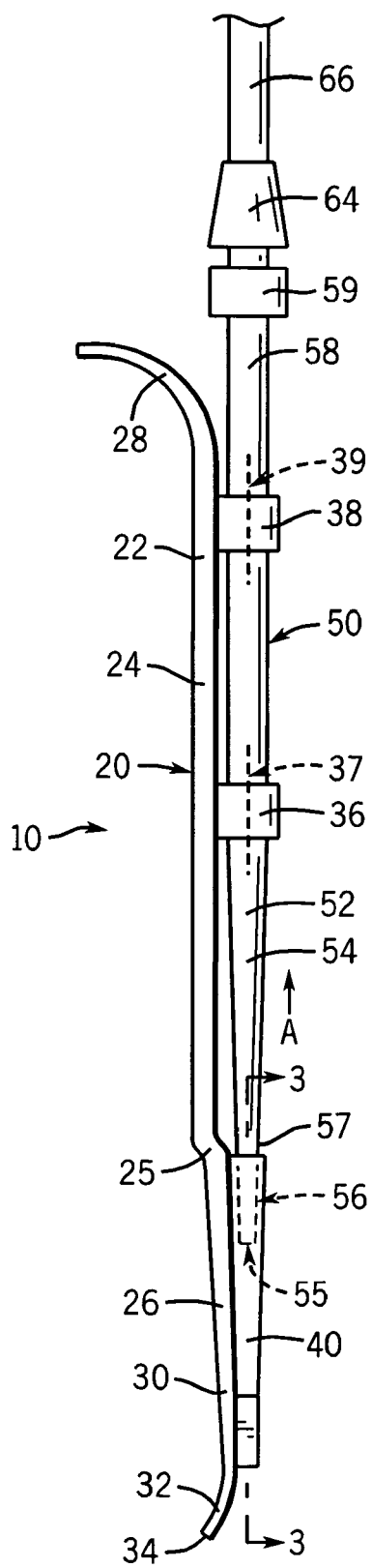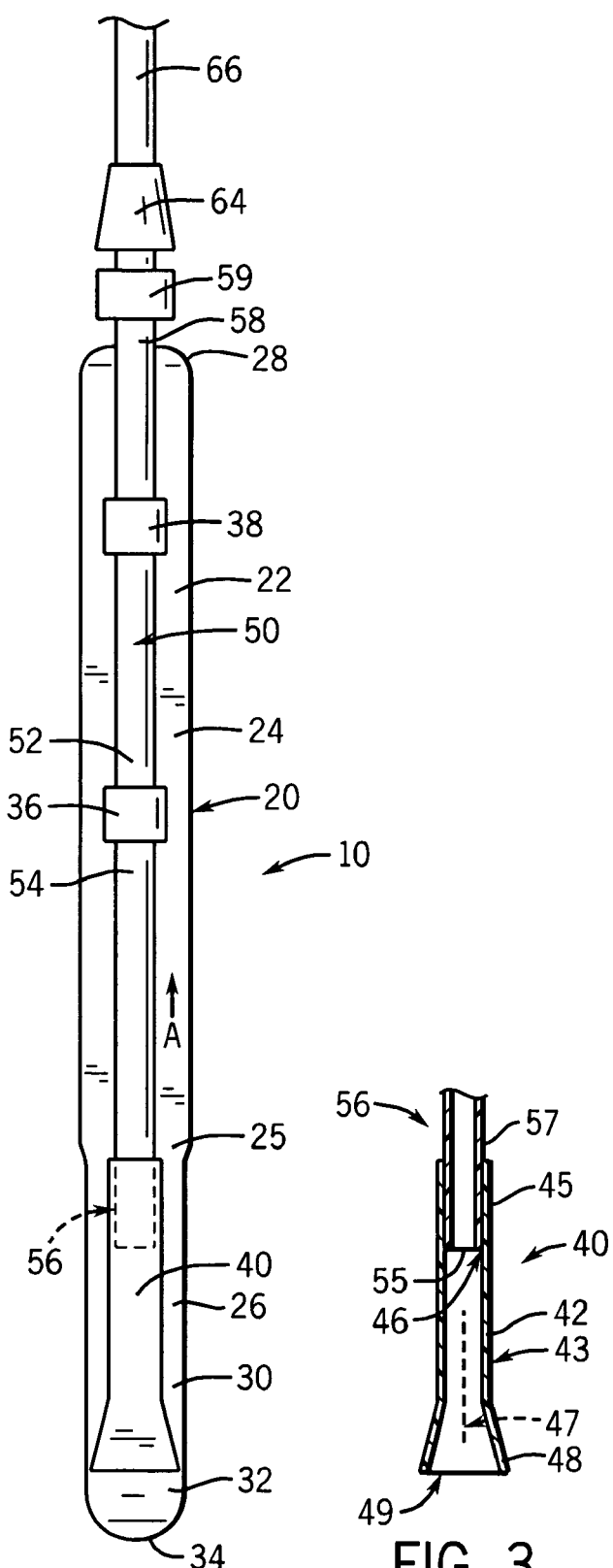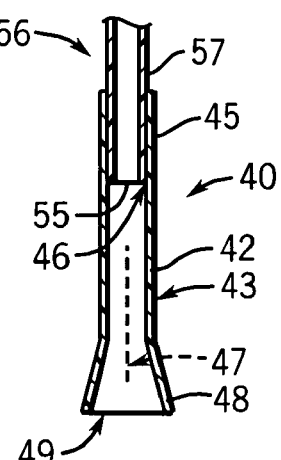

SUCTION RETRACTION INSTRUMENT FOR SURGERY

CROSS-REFERENCES TO RELATED APPLICATIONS

Not Applicable.

STATEMENT REGARDING FEDERALLY SPONSORED RESEARCH

Not Applicable.

BACKGROUND OF THE INVENTION

1. Field of the Invention

This invention relates to a combination suction retraction instrument for surgery.

2. Description of the Related Art

When oral surgery is being performed in a patient's mouth, it is necessary that the working area of the mouth be kept free of fluids and debris. These fluids may include saliva, blood, liquid used with drilling, and/or rinsing liquids, and the debris may be drilling dust and/or broken pieces of teeth. It is important for the patient's comfort to keep fluids from accumulating in the patient's mouth so that the fluids and debris are not swallowed and the patient can, if necessary, breath through his or her mouth.

Suction devices are used to keep the oral surgery work area clean and the patient's mouth relatively clear of fluids and debris. Such suction devices typically comprise a suction tube, which is connected to a long flexible hose, which is, in turn, connected to a vacuum source. When an oral surgeon is working on a tooth, an assistant is often required to manipulate the suction tube so as to maintain a clean work area and enable good visibility for the oral surgeon of the tooth being worked on. This procedure is problematic in that the assistant may be unable to anticipate the oral surgeon's moves in the patient's mouth and may thus be unable to keep the end of the suction tube out of the oral surgeon's way. As a consequence, the oral surgeon may prefer to do the evacuation of fluids and debris from the patient's mouth himself or herself.

During oral surgery, it is usually also necessary for the oral surgeon to use a retractor to push or pull soft tissue regions of the patient's mouth away from the work area. This may be necessary to provide a more unrestricted view of the work area. However, it is reported in U.S. Pat. No. 4,883,426 that problems can result when both tissue retraction and fluid evacuation are needed. For example, the working area of a patient's mouth may become crowded with dental implements to an extent that the oral surgeon's task becomes very difficult to perform. Moreover, it may be necessary for the oral surgeon to frequently and repeatedly shift between tissue retraction and fluid evacuation implements, thereby requiring a longer time for the surgery being performed. U.S. Pat. No. 4,883,426 seeks to solve this problem by providing a single dental implement which combines the features of a fluid evacuation device and a soft tissue retraction device. Combination suction retraction instruments have also been proposed in U.S. Pat. Nos. 6,875,173, 5,281,134, 5,123,403 and 4,049,000.

However, these devices do have drawbacks. When using these instruments, tissue, root tips, and bone may be drawn in to clog suction. For example, when an oral surgeon wishes to do deep socket exploration with an inseparable suction retraction device during surgery, the suction piece of the instrument can clog with tissue and debris thereby prolonging the surgical procedure.

Therefore, there is a need for a combination suction retraction instrument that serves the functions of: (1) minimizing the number of instruments in the surgeon's field of view, (2) maintaining a clear surgical field free from bone slurry, blood, saliva and irrigant, and (3) providing the utility for rapid separation of suction from retraction for independent suction use during deep socket exploration.

SUMMARY OF THE INVENTION

The foregoing needs are met by the present invention which provides a combination suction retraction instrument. The instrument includes a retractor having a body, a suction nozzle secured to a distal end of the body, and means for retaining a suction tube adjacent to the retractor. The means for retaining the suction tube is secured to the body of the retractor. The means for retaining the suction tube is structured to allow the suction tube to slide within the means for retaining the suction tube upon manual pulling of the suction tube by a surgeon. Also, the means for retaining the suction tube is structured such that the suction tube does not slide within the means for retaining the suction tube when manual pulling force is not exerted on the suction tube. In the instrument, a proximal end of the suction nozzle is dimensioned to engage a distal end of the suction tube in a sealing relationship thereby providing a suction flow path from an opening of the suction nozzle into the suction tube.

In one aspect of the invention, the means for retaining the suction tube may comprise a first round collar on the body of the retractor, and in another aspect of the invention, the means for retaining the suction tube further comprises a second round collar on the body of the retractor. The first collar may have a longitudinal axis colinear with a longitudinal axis of the proximal end of the suction nozzle, and the second collar may have a longitudinal axis colinear with the longitudinal axis of the proximal end of the suction nozzle. With this configuration of the first collar and the second collar, the suction tube may be threaded in a straight line though the first collar and the second collar into sealing interference fit engagement with the suction nozzle.

The distal end of the body of the retractor may have a curved tip region for retraction of tissue. The body of the retractor may have a curved proximal end opposite the distal end of the body for grasping of the proximal end by the surgeon. The suction nozzle may have a distal end opposite the proximal end of the suction nozzle, and the distal end of the suction nozzle may terminate inward from the curved tip region of the distal end of the body to slightly separate the suction and retraction regions of the instrument. The suction nozzle may have an outwardly flared distal end for improved suction of fluid and debris.

The invention also provides a suction retraction instrument including a suction tube having a distal end and having a proximal end suitable for attachment to a suction hose that is connected to a vacuum source. The instrument includes a retractor including a body, a suction nozzle secured to a distal end of the body, and means for retaining the suction tube adjacent the retractor. The means for retaining the suction tube is secured to the body. The means for retaining the suction tube is structured to allow the suction tube to slide within the means for retaining the suction tube upon manual pulling of the suction tube by a surgeon. Also, the means for retaining the suction tube is structured such that the suction tube does not slide within the means for retaining the suction tube when manual pulling force is not exerted on the suction tube. In the instrument, a proximal end of the suction nozzle is dimensioned to engage a distal end of the suction tube in a sealing relationship thereby providing a suction flow path from an opening of the suction nozzle into the suction tube. In one form, the distal end of the suction tube terminates in an opening, and an outer surface of the distal end of the suction tube tapers inward toward the opening. This provides for easier insertion of the suction tube into the proximal end of the suction nozzle.

Thus, it is an advantage of the present invention to provide an improved combination suction retraction instrument that may be used for deep socket exploration during oral surgery.

These and other features, aspects, and advantages of the present invention will become better understood upon consideration of the following detailed description, drawings, and appended claims.

BRIEF DESCRIPTION OF THE DRAWINGS

FIG. 1 is a right side elevational view of a combination suction retraction instrument according to the invention.

FIG. 2 is a front elevational view of the instrument of FIG. 1.

FIG. 3 is a partial cross-sectional view of the instrument of FIG. 1 taken along line 3-3 of FIG. 1.

Like reference numerals will be used to refer to like parts from Figure to Figure in the following description of the drawings.

DETAILED DESCRIPTION

Figure 4:
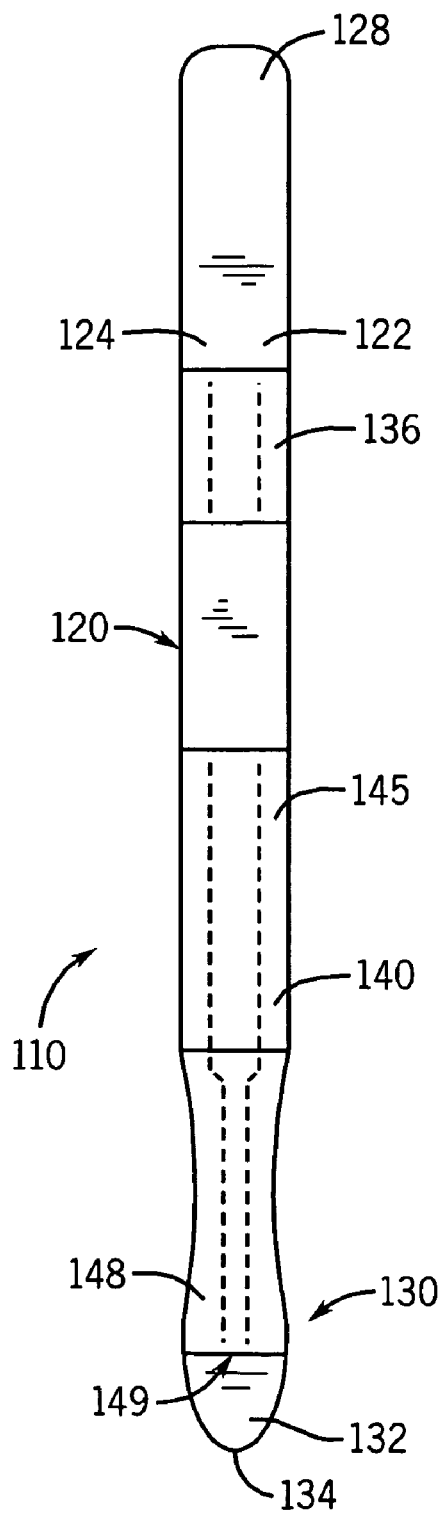
FIG. 4 is a front elevational view of a combination suction retraction instrument according to a second embodiment of the invention.

Turning to FIGS. 1 to 3, there is shown a combination suction retraction instrument 10 according to the invention. The instrument 10 includes a retractor 20 having a body 22. Preferably, the retractor 20 is formed from stainless steel. However, other metallic materials, ceramic materials, composite materials or polymeric materials would also be suitable for forming the retractor 20. The body 22 has a first generally flat section 24, a second generally flat section 26, and an angled junction 25 that joins the first section 24 and the second section 26 in an offset configuration. A transverse cross section of each of the first section 24, the angled junction 25 and the second section 26 is typically rectangular. It can be seen from FIG. 2 that the second section 26 has a reduced width compared to the first section 24. In one embodiment, the width of the first section 24 is about 0.5 inches, the overall length of the retractor is about 6.3125 inches, and the thickness of the retractor is about 0.242 inches.

The body 22 of the retractor 20 has a distal end 30 that terminates in a curved tip region 32 that has a distal arcuate edge 34. The curved tip region 32 and distal arcuate edge 34 allow the surgeon to retract tissue during surgery. The second section 26 of the body 22 of the retractor 20 terminates in a proximal end 28 that is curved in an approximately 90 degree arc that provides a convenient grasping surface for the surgeon.

The retractor 20 includes means for retaining a suction tube 50 adjacent the retractor 20. An example means for retaining the suction tube is shown in FIGS. 1 and 2. The means for retaining the suction tube includes a first round collar 36 and a second round collar 38 that are secured to a surface of the body 22 of the retractor 20. The first collar 36 has a longitudinal axis 37 and the second collar 38 has a longitudinal axis 39. The first collar 36 and the second collar 38 retain the suction tube 50 adjacent the retractor 20 as described below. In certain embodiments, the second collar 38 is not present. Other structures, such as opposed arcs, may be used for retaining the suction tube.

The retractor 20 also includes a suction nozzle 40 secured to the distal end 30 of the body 22 of the retractor 20. The suction nozzle 40 may be permanently or removably secured to the body 22 of the retractor 20. The suction nozzle 40 has a tubular body 42 with an outer surface 43. The suction nozzle 40 has a proximal end 45 with an inside surface 46 and a longitudinal axis 47. The suction nozzle 40 also has a distal flared end 48 with an opening 49 for keep the oral surgery work area clean and the patient's mouth relatively clear of fluids and debris. In the embodiment shown, the distal end 48 of the suction nozzle 40 terminates inward from the curved tip region 32 of the distal end 30 of the body 22 of the retractor 20. Thus, the suction nozzle 40 is secured to a flat section of the retractor 20. Also, in the embodiment shown the suction nozzle 40 is formed from stainless steel. However, polymeric materials, ceramic materials or composite materials are also suitable for forming the nozzle 40.

The suction retraction instrument 10 also includes a suction tube 50 having a tubular body 52. The suction tube 50 is preferably formed from stainless steel. The suction tube 50 has a central section 54, a distal end 56 with an outer surface 57 and an opening 55, and proximal end 58. A fitting 59 is secured to the proximal end 58 of the suction tube 50. The fitting 59 is secured to a suction hose fitting 64 of a flexible suction hose 66 that is connected to a conventional vacuum source (not shown).

The suction tube 50 is removably attached to the retractor 20 as follows. First, the distal end 56 of the suction tube 50 is inserted into the second collar 38 of the retractor 20. Second, the distal end 56 of the suction tube 50 is inserted into the first collar 36 of the retractor 20. Third, the distal end 56 of the suction tube 50 is inserted into the proximal end 45 of the suction nozzle 40 to create a friction (interference) fit seal between the outer surface 57 of the distal end 56 of the suction tube 50 and the inside surface 46 of the proximal end 45 of the suction nozzle 40.

In one preferred embodiment, the longitudinal axis 39 of the second collar 38 and the longitudinal axis 37 of the first collar 36 are colinear with the longitudinal axis 47 of the proximal end 45 of the suction nozzle 40 such that insertion of the suction tube 50 in the second collar 38, the first collar 36 and the proximal end 45 of the suction nozzle 40 proceeds along a linear path. In another preferred embodiment, the outer surface 57 of the distal end 56 of the suction tube 50 tapers inward toward the distal opening 55 of the suction tube 50. The reduced outside diameter at the outer surface 57 of the distal end 56 of the suction tube 50 near the distal opening 55 provides for easier insertion of the distal end 56 of the suction tube 50 into the proximal end 45 of the suction nozzle 40.

The first collar 36, the second collar 38 and the proximal end 45 of the suction nozzle 40 each have internal dimensions such that a friction (interference) fit is formed between the first collar 36, the second collar 38 and the proximal end 45 of the suction nozzle 40. However, upon application of a manual pulling force on the suction tube 50 or the fitting 59 of the suction tube 50 directed away from the retractor 20 by the surgeon, the suction tube 50 may slide in the first collar 36, the second collar 38 and the proximal end 45 of the suction nozzle 40.

An oral surgeon may use the combination suction retraction instrument 10 as follows. First, the suction tube 50 is attached to the suction hose fitting 64 of the suction hose 66 that is connected to a conventional vacuum source. The suction tube 50 is then threaded through the second collar 38 (if present) and the first collar 36 and into the proximal end 45 of the suction nozzle 40. The oral surgeon may then use the suction retraction instrument 10 (i) for removal of fluids and debris from a patient's mouth through the suction nozzle 40 and (ii) for retraction of tissue with the curved tip region 32 and distal arcuate edge 34 of the retractor 20.

If the oral surgeon wishes to perform only retraction and avoid suctioning vital structures such as nerve, muscle and fat, the oral surgeon pulls on the suction tube 50 or the fitting 59 of the suction tube 50 in a direction away from the retractor 20. The suction tube 50 then slides out of the suction nozzle 40 in direction "A" of FIGS. 1 and 2. The suction tube 50 may be pulled away from the suction nozzle 40 any distance desired. For example, the opening 55 of the distal end 56 of the suction tube 50 may be pulled back to near the first collar 36. Suction is therefore interrupted through the suction nozzle 40 and retraction without suction can be performed.

After completion of deep socket exploration, the oral surgeon may wish to perform suction again. The suction tube 50 is therefore reinserted into the proximal end 45 of the suction nozzle 40. The oral surgeon may then use the suction retraction instrument 10 (i) for removal of fluids and debris from a patient's mouth through the suction nozzle 40 and (ii) for retraction of tissue with the curved tip region 32 and distal arcuate edge 34 of the retractor 20.

Figure 5:
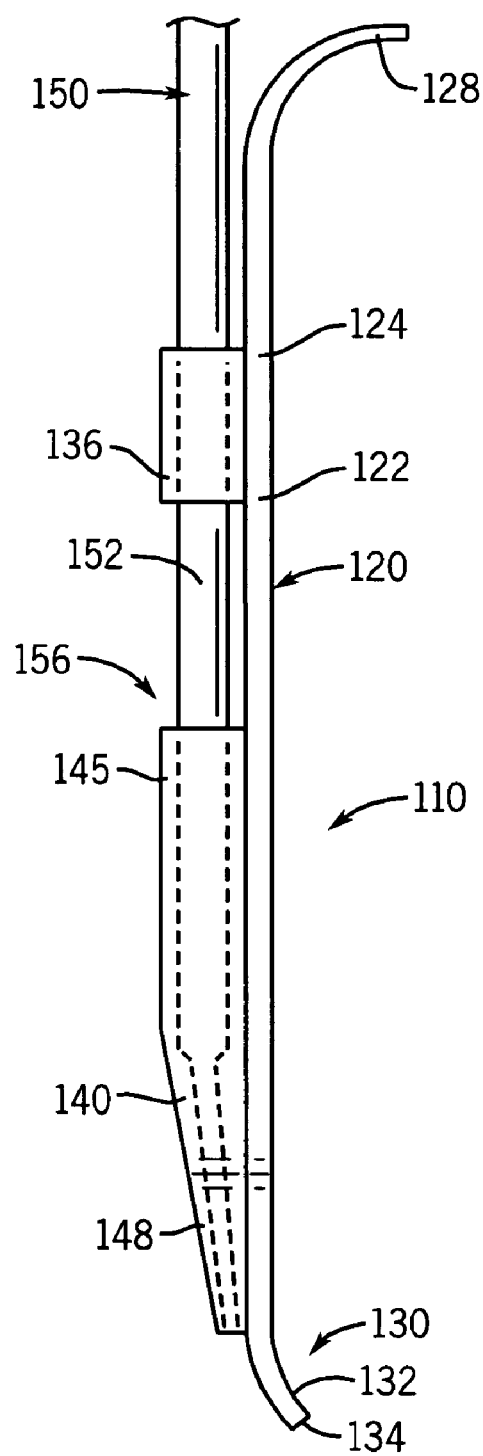
FIG. 5 is a left side elevational view of the instrument of FIG. 4.

Turning to FIGS. 4 and 5, there is shown a second embodiment of a combination suction retraction instrument 110 according to the invention. The instrument 110 includes a retractor 120 having a body 122. Preferably, the retractor 120 is formed from stainless steel. However, other metallic materials, ceramic materials, composite materials or polymeric materials would also be suitable for forming the retractor 120. The body 122 has a generally flat section 124 with a transverse cross section that is typically rectangular. It can be seen from FIG. 4 that the section 124 has a reduced width at its lower end.

The body 122 of the retractor 120 has a distal end 130 that terminates in a curved tip region 132 that has a distal arcuate edge 134. The curved tip region 132 and distal arcuate edge 134 allow the surgeon to retract tissue during surgery. The upper section of the body 122 of the retractor 120 terminates in a proximal end 128 that is curved in an approximately 90 degree arc that provides a convenient grasping surface for the surgeon.

The retractor 120 includes means for retaining a suction tube 150 adjacent the retractor 120. An example means for retaining the suction tube is shown in FIGS. 4 and 5. The means for retaining the suction tube includes a tubular collar 136 that is secured to a surface of the body 122 of the retractor 120. The collar 136 retains the suction tube 150 adjacent the retractor 120 as described below.

The retractor 120 also includes a suction nozzle 140 secured to the distal end 130 of the body 122 of the retractor 120. The suction nozzle 140 may be permanently or removably secured to the body 122 of the retractor 120. The suction nozzle 140 has a proximal end 145. The suction nozzle 140 also has a distal end 148 with an opening 149 for keep the oral surgery work area clean and the patient's mouth relatively clear of fluids and debris. In the embodiment shown, the distal end 148 of the suction nozzle 140 terminates inward from the curved tip region 132 of the distal end 130 of the body 122 of the retractor 120. Thus, the suction nozzle 140 is secured to a flat section of the retractor 120. Also, in the embodiment shown the suction nozzle 140 is formed from stainless steel. However, polymeric materials, ceramic materials or composite materials are also suitable for forming the nozzle 140.

The suction retraction instrument 110 also includes a suction tube 150 (shown in FIG. 5) having a tubular body 152. The suction tube 150 is preferably formed from stainless steel. The suction tube 150 is removably attached to the retractor 120 as follows. First, the distal end 156 of the suction tube 150 is inserted into the collar 136 of the retractor 120. Second, the distal end 156 of the suction tube 150 is inserted into the proximal end 145 of the suction nozzle 140 to create a friction (interference) fit seal between the outer surface of the distal end 156 of the suction tube 150 and the inside surface of the proximal end 145 of the suction nozzle 140. The collar 136 and the proximal end 145 of the suction nozzle 140 each have internal dimensions such that a friction (interference) fit is formed between the collar 136 and the proximal end 145 of the suction nozzle 140. However, upon application of a manual pulling force on the suction tube 150 directed away from the retractor 120 by the surgeon, the suction tube 150 may slide in the collar 136 and the proximal end 145 of the suction nozzle 140.

Thus, the present invention provides a combination suction retraction instrument that may be used for oral surgery. When using the instrument, an assistant need not provide suction during the surgery. If the oral surgeon wishes to perform only retraction and avoid suctioning vital structures such as nerve, muscle and fat, the suction and retraction components can be quickly separated.

Although the present invention has been described with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A suction retraction instrument comprising:
   a suction tube having a distal end and having a proximal end suitable for attachment to a suction hose;
   a retractor including a body extending along an outside of the suction tube;
   a suction nozzle secured to a distal end of the body; and
   means for retaining the suction tube adjacent the retractor, the means for retaining being secured to the body, the means for retaining being dimensioned to allow the suction tube to slide within the means for retaining upon manual pulling of the suction tube,
   wherein a proximal end of the suction nozzle is dimensioned to engage the distal end of the suction tube in a sealing relationship, and
   wherein the suction tube has a first position in which the distal end of the suction tube seals with the suction nozzle at the distal end of the body, and
   wherein the suction tube has a second position in which the distal end of the suction tube is near the means for retaining thereby interrupting suction through the suction nozzle.

2. The instrument of claim 1, wherein:
   the distal end of the suction tube terminates in an opening, and an outer surface of the distal end of the suction tube tapers inward toward the opening.

3. The instrument of claim 1, wherein:
   the means for retaining comprises a collar.

4. The instrument of claim 3, wherein:
the collar has a longitudinal axis colinear with a longitudinal axis of the proximal end of the suction nozzle.

5. The instrument of claim 3, wherein:
the means for retaining further comprises a second collar, the second collar being dimensioned to retain the suction tube adjacent the retractor, and the second collar also being dimensioned to allow the suction tube to slide within the second collar upon manual pulling of the suction tube.

6. The instrument of claim 5, wherein:
the collar has a longitudinal axis colinear with a longitudinal axis of the proximal end of the suction nozzle, and
the second collar has a longitudinal axis colinear with the longitudinal axis of the proximal end of the suction nozzle.

7. The instrument of claim 1, wherein:
the distal end of the body has a curved tip region.

8. The instrument of claim 7, wherein:
the suction nozzle has a distal end opposite the proximal end of the suction nozzle, and
the distal end of the suction nozzle terminates inward from the curved tip region of the distal end of the body.

9. The instrument of claim 1, wherein:
the body has a curved end opposite the distal end of the body.

10. The instrument of claim 1, wherein:
the suction nozzle has an outwardly flared distal end opposite the proximal end of the suction nozzle.

11. The instrument of claim 1, wherein:
the proximal end of the suction nozzle engages the first end of the suction tube in a friction fit.

12. The instrument of claim 1, wherein:
the body has a proximal end that laterally extends outwardly from the body thereby defining a grasping surface.

13. The instrument of claim 12, wherein:
the means for retaining comprises a collar, and
the collar is secured to a surface of the body between the proximal end of the body and the distal end of the body.

14. The instrument of claim 1, wherein:
the means for retaining comprises a collar, and
the collar is secured to a surface of the body.

\* \* \* \* \*